(12) United States Patent
Preuss et al.

(10) Patent No.: US 9,301,855 B2
(45) Date of Patent: Apr. 5, 2016

(54) INSERTION INSTRUMENT FOR INSERTING SOCKET INSERTS INTO THE SPHERICAL RECESSES OF HIP SOCKETS

(75) Inventors: Roman Preuss, Kirchheim unter Teck (DE); Michael Kuntz, Homburg (DE); Tobias Weiss, Ebersbach (DE); Ralph Autenrieth, Esslingen (DE); Götz Griesmayr, Winterbach (DE); Manuela Muhr-Schenk, Fellbach (DE)

(73) Assignee: CeramTec GmbH, Plochingen (DE)

( * ) Notice: Subject to any disclaimer, the term of this patent is extended or adjusted under 35 U.S.C. 154(b) by 215 days.

(21) Appl. No.: 13/139,436

(22) PCT Filed: Dec. 15, 2009

(86) PCT No.: PCT/EP2009/067135
§ 371 (c)(1),
(2), (4) Date: Jun. 21, 2011

(87) PCT Pub. No.: WO2010/069940
PCT Pub. Date: Jun. 24, 2010

(65) Prior Publication Data
US 2011/0245837 A1 Oct. 6, 2011

(30) Foreign Application Priority Data
Dec. 17, 2008 (DE) .......................... 10 2008 054 825

(51) Int. Cl.
*A61B 17/56* (2006.01)
*A61F 2/46* (2006.01)
*A61F 2/34* (2006.01)
*A61F 2/30* (2006.01)

(52) U.S. Cl.
CPC ................ *A61F 2/4637* (2013.01); *A61F 2/34* (2013.01); *A61F 2002/302* (2013.01); *A61F 2002/30332* (2013.01); *A61F 2002/30565* (2013.01); *A61F 2220/0033* (2013.01); *A61F 2230/0065* (2013.01)

(58) Field of Classification Search
USPC ................... 623/22.12; 606/91, 99; 81/53.12; 267/150, 161; 439/574, 575; 24/295; 248/74.2, 229.16, 510
See application file for complete search history.

(56) References Cited

U.S. PATENT DOCUMENTS

| | | | | |
|---|---|---|---|---|
| 2,123,458 A | * | 7/1938 | Woehler et al. | 52/718.02 |
| 2,798,271 A | * | 7/1957 | Flora | 248/500 |
| 6,468,281 B1 | * | 10/2002 | Badorf et al. | 606/91 |
| 6,589,284 B1 | * | 7/2003 | Silberer | 623/22.29 |
| 2005/0211859 A1 | * | 9/2005 | Schultz | 248/230.1 |
| 2008/0087782 A1 | * | 4/2008 | Sutherland et al. | 248/231.9 |
| 2009/0120350 A1 | * | 5/2009 | Tamez, Jr. | 116/205 |

* cited by examiner

*Primary Examiner* — Christian Sevilla
(74) *Attorney, Agent, or Firm* — Norton Rose Fulbright US LLP

(57) ABSTRACT

An insertion instrument for hip endoprosthetics for inserting socket inserts into endoprosthetic hip sockets having holding claws which are connected to a substantially ring-shaped support element through spring elements, wherein the insertion instrument can be placed on the socket insert and can be connected to said socket insert through the holding claws. In order for the user to receive direct palpatory information about the events in the operation areas and to not suffer a perceived loss of control, it is proposed that the support element surround a freely accessible, substantially circular effective insertion area, the center point of which is located on the longitudinal axis of the insertion instrument.

13 Claims, 6 Drawing Sheets

(A-A)

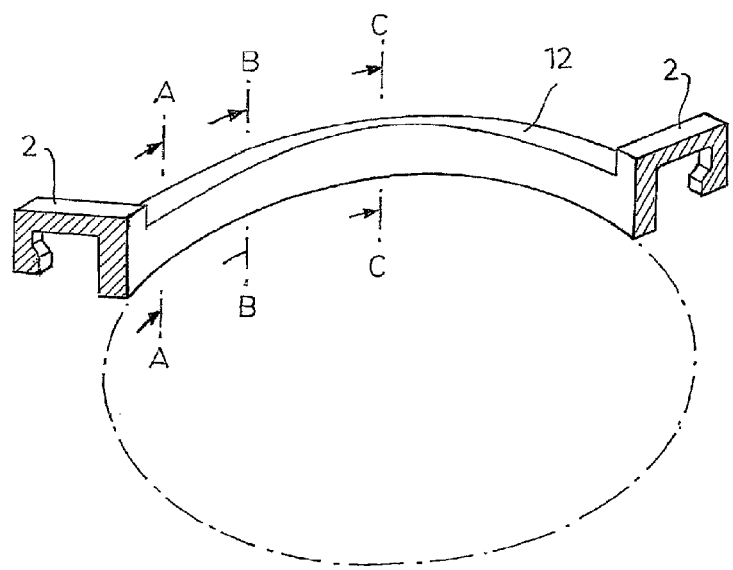
Fig.10
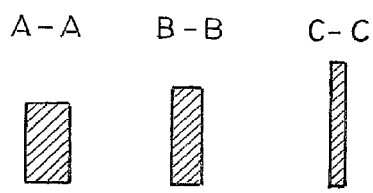

INSERTION INSTRUMENT FOR INSERTING SOCKET INSERTS INTO THE SPHERICAL RECESSES OF HIP SOCKETS

RELATED APPLICATIONS

This application is a §371 application of PCT/EP2009/067135 filed Dec. 15, 2009, which claims priority from German Patent Application No. 10 2008 054 825.1 filed Dec. 17, 2008.

FIELD OF THE INVENTION

The invention relates to an insertion instrument for the hip endoprosthesis for inserting socket inserts into endoprosthetic hip sockets as described herein.

BACKGROUND OF THE INVENTION

There exist on the market a large number of prosthesis systems for replacing the natural hip joint in the event of painful, traumatic, arthrotic or other changes. Generally, so-called modular systems are used in which there is inserted into a hip socket, which generally comprises a metal alloy, a socket insert which forms a portion of the artificial sliding bearing and which may comprise a metal alloy, a ceramic material, a plastics material or a composite of the above-mentioned materials. The connection between the socket insert and the hip socket is often brought about by means of a so-called conical clamping, wherein a cone-like portion of the external geometry of the socket insert forms a frictionally engaged connection with a correspondingly cone-like portion of the internal geometry of the hip socket, cf. FIG. 1.

FIG. 1 is a sectional illustration of a hip socket (hashed) according to the prior art with an inserted socket insert which is connected to the hip socket via a conical clamping action.

One of the problems which may occur intra-operatively is the skewed insertion of the socket insert into the hip socket. Jamming of the socket insert between three contact points within the clamping cone of the hip socket may then occur in place of the conical clamping described. In accordance with the magnitude of the force applied during clamping, such high frictional forces occur as a result of the point-like jamming that the position of the socket insert can no longer be corrected intra-operatively, cf. FIG. 2.

FIG. 2 is a sectional illustration of a hip socket (hashed) according to the prior art with a socket insert inserted in a skewed manner.

The consequences for the function of the hip joint prosthesis with the socket insert inserted in a pivoted manner substantially depend on the material of the socket insert and range from increased wear and corrosion to complete destruction of the socket insert. For instance, a socket insert inserted in a skewed manner may be the cause of a subsequent complex, painful and expensive revision operation.

In order to prevent the skewed insertion of socket inserts, a range of insertion instruments are commercially available. Their operation is substantially based on the following three steps:

1. Gripping the socket insert at the upper outer edge.
2. Orienting the instrument with the socket insert in relation to the hip socket so that the axes of symmetry of the hip socket and socket insert extend in parallel.
3. Abruptly and rapidly pushing the socket insert into the hip socket, with the gripping retention being disengaged and the clamping connection being produced.

The upper outer edge of the socket insert is gripped by the instrument generally by means of a so-called three-point fixing arrangement. To that end, the instrument has claw-like elements which project beyond the outer edge of the socket insert at least at three points and apply a normal force or friction force to a point-like location below the front face of the socket insert.

The orientation of the instrument with the socket insert is generally carried out by positioning the instrument on the front face of the hip socket or on elements (for example, recesses or protrusions) near the front face which are again in a plane parallel with the front face.

The abrupt ejection of the socket insert out of the gripper elements, with a clamping action being produced between the socket insert and the hip socket, is generally carried out by an additional ram on the insertion instrument or using a so-called impactor instrument.

Such insertion instruments are described, for example, in EP 1076537 B1 and DE 29922792 U1.

Disadvantages of the existing solutions are as follows:

the insertion of the socket insert into the hip socket and the production of the initial jamming are carried out by a ram or an impactor instrument. Both result in the operating surgeon not having any finger contact with the socket insert and consequently losing some control over the movement of the component. This is generally perceived by surgeons, who establish a substantial portion of their information concerning their operating field by palpation, to be very unpleasant and has a low level of acceptance (=use) for the insertion instruments as a result.

Using an insertion instrument is in most cases an additional operating step which results in a low level of acceptance for the insertion instruments owing to the pressure to increase efficiency in the operating theatre.

Insertion instruments which are supported on the entire front face of the hip socket in order to orientate the socket insert can be impeded during orientation by bone tissue and soft tissue which projects from the outer side over the edge of the hip socket so that it is impossible to insert the socket insert with the instrument without skewing, or the risk of skewing is again increased.

The insertion instrument is often an additional instrument in the set of instruments of the surgeon, which involves additional costs in providing the operating instruments.

Insertion instruments which are not an additional instrument in the set of instruments but which are intended for single use are either supplied as separate products (=additional packaging causes additional time for unpacking and additional waste) or require a specific construction for the packaging of the socket insert in order also to accommodate the insertion instrument therein.

SUMMARY OF THE INVENTION

The problems described are solved by an insertion instrument according to the invention according to the features of the present invention.

BRIEF DESCRIPTION OF THE FIGURES

FIG. 10 shows an insertion instrument according to the invention (cut-out between two holding claws) having a varying annular cross-section—variation in height and width of the cross-section to produce flexurally more rigid and flexurally less rigid zones.

DETAILED DESCRIPTION

The insertion of socket inserts into endoprosthetic hip sockets and anchoring at that location by means of conical clamping are carried out with an insertion instrument according to the invention which is positioned on the front face of the socket insert and which is clampingly connected thereto by means of holding claws. For insertion, the socket insert with the insertion instrument positioned thereon is inserted into the endoprosthetic hip socket without any mutual contact at that time and positioned. Subsequently, the socket insert slides out of the holding claws of the insertion instrument owing to pressure on the socket insert or the spherical recess of the socket insert with sufficient connection force and engages with the hip socket with frictionally engaged contact.

The insertion instrument is used only to grip and to accurately position the socket insert in the hip socket. The pressure on the inner spherical recess of the socket insert until the connection force is sufficient is brought about without any pressure transmission devices directly and exclusively by the fingers of the user. The disadvantages described are thereby overcome and the surgeon or user receives direct tactile information regarding occurrences in the field of operation and does not suffer any perceived loss of control.

The insertion instrument according to the invention is characterised in that the support element surrounds a freely accessible, effective penetration face which is substantially circular and whose centre point is on the longitudinal axis of the insertion instrument. The substantially circular, effective penetration face must be large enough for a finger of the user or surgeon to be able to fit through. The penetration face must be so small that the insertion instrument has adequate stability and, on the other hand, must not be so small that fingers of the user cannot be fitted through.

In a preferred embodiment, the effective diameter of the penetration face is greater than or equal to 2.0 cm, particularly preferably greater than or equal to 2.5 cm.

Figure 3:
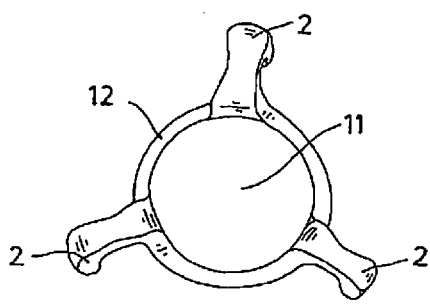
FIG. 3 shows an insertion aid according to the invention.
Figures 7A, 7B:
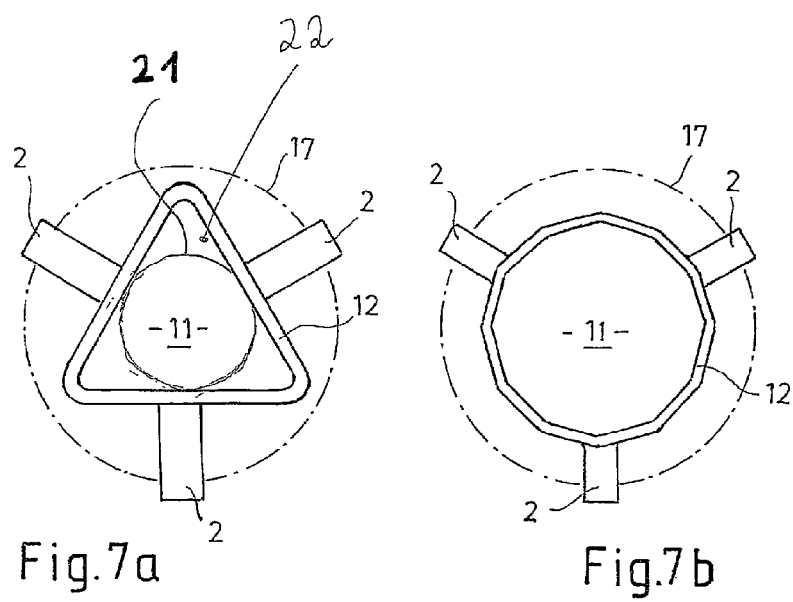
FIGS. 7a and 7b show two different insertion instruments when viewed from above; it is possible to vary the geometry of the annular, resilient element, for example, by means of a triangular shape (FIG. 7a) or a polygonal shape (FIG. 7b).
Figure 8:
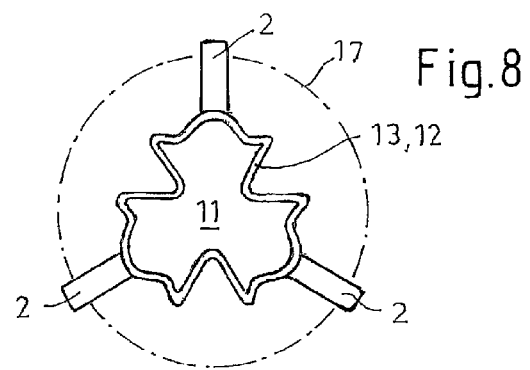
FIG. 8 is a plan view of an insertion instrument according to the invention having a direct connection of the three holding claws with concertina-like resilient elements or resilient support elements or connection paths between the claws.

The term effective diameter is intended to refer to the diameter of the circle in a support element that encloses a circle as a penetration face (cf. FIG. 3). However, if the support element surrounds a penetration face which is different from a circle, as illustrated in FIGS. 7a, 7b and 8, the diameter of the inscribed circle (cf. FIG. 7a, reference numeral 20) is intended to be understood by the effective diameter. The term effective diameter is intended to be understood to be the diameter which is significant for the finger of the user and not the region (cf. FIG. 7a, reference numeral 21) of the penetration face that is substantially insignificant for the insertion of the finger.

In an inventive construction, the resilient elements and the support element are combined to form an integral resilient support element and the holding claws are arranged on the resilient support element. In that embodiment, the insertion instrument is integral and is easy to produce.

The resilient support element is preferably a resiliently flexible ring, the holding claws being arranged on the outer periphery of the ring. For positioning on the outer edge of the socket insert, the holding claws only have to be pushed by radial expansion over the outer edge of the socket insert, that is to say, the resilient support element is deformed and a resilient force acts on the holding claws. Consequently, each holding face of the holding claws applies a pressing force to the socket insert, which force is equal to the resilient force on the holding claw in terms of magnitude and direction, respectively.

In another inventive construction, the resilient support element has a triangular shape or polygonal shape. A concertina-like shape may also be advantageous. It should always be ensured that the effective penetration face is large enough for a finger to be able to be fitted through. The resilient force can be adjusted by the formation of the shape of the resilient support element.

In an alternative embodiment, the support element and the resilient elements are separate components and the holding claws are connected to the support element by means of the resilient elements. The resilient forces can be adapted individually by the resilient elements being selected in a suitable manner.

In one embodiment, the resilient elements have a concertina-like shape which is preferably arranged perpendicularly relative to the plane of the holding claws. Alternatively, the resilient support element or the support elements have a cross-section which varies in terms of the height and width thereof between the holding claws in order to produce flexurally more rigid and flexurally less rigid zones.

The resilient support element or the support elements can also have a change in the cross-sectional geometry between the holding claws in order to produce flexurally more rigid and flexurally less rigid zones.

The invention is explained in greater detail below with reference to Figures.

Figure 1:
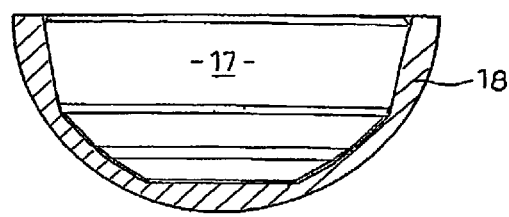
FIG. 1 is a sectional illustration of a hip socket of the prior art.
Figure 2:
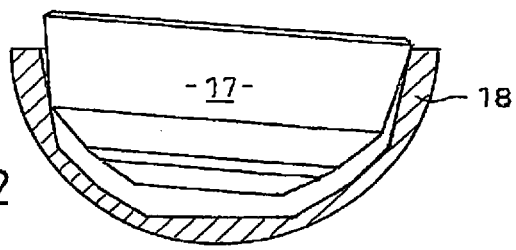
FIG. 2 is a sectional illustration of a hip socket according to the prior art with a socket inserted in a skewed manner.

With regard to FIGS. 1 and 2, which show the prior art, reference is made to the introduction to the description.

FIG. 3 shows an insertion aid according to the invention comprising an annular, flexible resilient support element 12 having holding claws 2.

In this embodiment, the insertion instrument comprises a flexible, annular resilient support element 12, which three holding claws 2 adjoin. The insertion instrument is advantageously constructed from a technical perspective relating to production as a monolithic component which can be produced, for example, by injection moulding. The resilience of the resilient support element 12 results in the holding claws 2 being able to be displaced radially. The resilient force to be overcome increases with increasing radial displacement of the holding claws 2. The force/path characteristic of the holding claws 2 can be influenced by corresponding geometric formation of the annular resilient support element 12.

Figure 4:
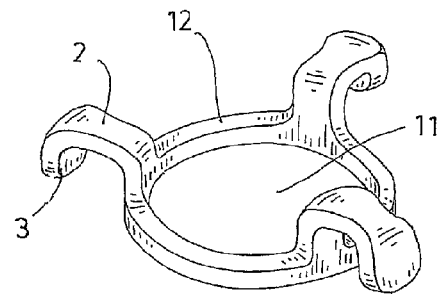
FIG. 4 shows an insertion aid according to the invention having a visible holding face.

The holding claws 2 each have a holding face 3 (cf. FIG. 4). In the assembled state the holding claws 2 are positioned with their lower end 6 on an outer face of the socket insert 17 (cf. FIG. 6). In the assembled state, the resilient support element 12 is in the spherical recess 5 of the socket insert 17 and the holding claws 2 engage over the front face and outer edge of the socket insert 17. However, embodiments in which the resilient support element 12 and the holding claws 2 are in a plane above the spherical recess 5 of the socket insert 17 are also conceivable.

FIG. 4 shows an insertion aid according to the invention having a visible holding face 3.

According to the invention, the insertion instrument has such dimensions that the holding claws 2 can only be fitted over the outer edge of the socket insert 17 by being radially expanded. That is to say, the resilient support element 12 is deformed and a resilient force acts on the holding claws 2. Consequently, each holding face 3 applies to the socket insert 17 a pressing force which is equal to the resilient force at the holding claw 2 in terms of magnitude and direction. Owing to the pressing forces, friction forces which act counter to the insertion instrument being drawn away from the socket insert 17 also act between the holding faces 3 and the outer face of the socket insert 17. This is important for the operation of the insertion instrument.

Figure 5:
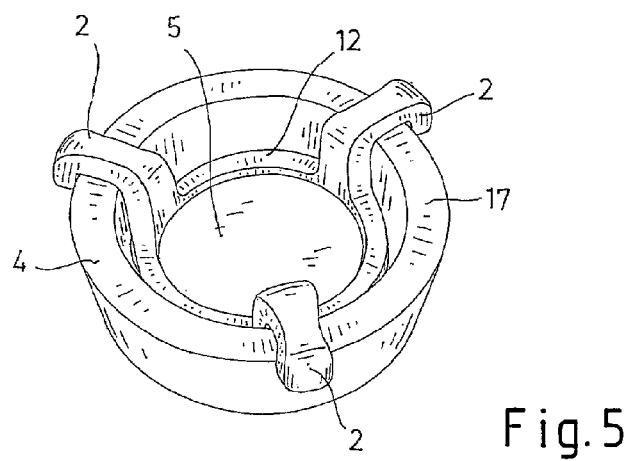
FIG. 5 shows a socket insert with an insertion instrument according to the invention in an assembled state.

FIG. 5 shows a socket insert 17 with an insertion instrument according to the invention in the assembled state.

If the socket insert 17 with an insertion instrument assembled is pushed into a hip socket 18, the holding claws 2 move into contact at their lower end 6 with the front face of the hip socket 18. Since the holding claws 2 all have the same extent in a downward direction, the contact points form a plane which is parallel with both the front face of the hip socket 18 and the front face of the socket insert 17. Consequently, orientation of the two front faces is thereby also brought about so that they are parallel with each other. Possible skewing of the socket insert 17 is thereby counteracted. Slight displacement of the socket insert 17 in the hip socket 18 is possible owing to the lateral gap which still exists at this time between the socket insert 17 and the hip socket 18. By pushing the socket insert 17 back and forth repeatedly in the hip socket 18—until stopping lightly in each case—with the finger 7, it is possible for the user to check the correct position of the socket insert 17 in the hip socket 18. Above all the provision of slight displaceability and the stopping of the components provide the user with very good tactile feedback concerning the correct position of the socket insert 17 in the hip socket 18.

In order finally to push the socket insert into the hip socket 18 as far as frictionally engaged contact between the two cone faces—externally on the socket insert 17 and internally on the hip socket 18—the friction forces between the holding faces 3 of the insertion instrument and the outer face of the socket insert 18 have to be overcome. This is brought about by continuously increasing, or preferably by abruptly increasing, the axial connection force by the finger 7 of the user. The socket insert 17 travels over the short path remaining and slides into the hip socket 18, substantial skewing of the socket insert 17 no longer being possible. Possible slight skewing actions are compensated for and corrected by the self-centring action of the conical clamping connection.

Figure 6:
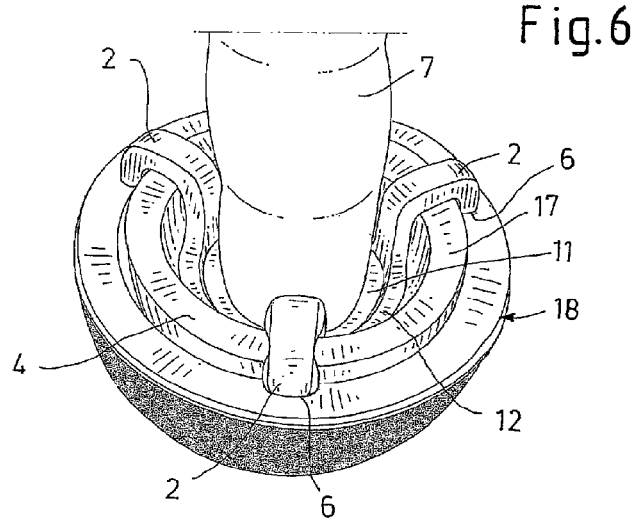
FIG. 6 shows a socket insert having an insertion instrument according to the invention in the assembled state during insertion of the socket insert into the hip socket.

FIG. 6 shows a socket insert 17 having an insertion instrument according to the invention in the assembled state during insertion of the socket insert 17 into the hip socket 18.

As soon as the holding claws 2 have disengaged from the socket insert 17, the resilient element or the resilient support element 12 moves back into its initial shape. Owing to that rapid restoring movement, the insertion instrument is further pressed away from the front face of the hip socket 18 and slides a few centimeters along the finger 7 of the user until the movement of the insertion instrument stops. If the user wears latex gloves, as necessarily provided for during operations, the insertion instrument remains suspended on the finger of the user owing to the glove. The user thereby necessarily removes the insertion instrument from the operating field if he takes his hand out of the operating field.

The advantages of the construction according to the invention involve:
the direct handling of the socket insert 17 during insertion using the fingers 7 of the user (surgeon) so that the user receives direct tactile information concerning occurrences in the operating field and does not suffer any perceived loss of control;
the three-point fixing arrangement by means of the holding claws 2 on the front face of the hip socket 18 which is obtained by using three holding claws 2 and consequently results in static certainty when the components are orientated relative to each other. Should portions of the front face of the hip socket 18 be concealed by protruding tissue, however, it is also sufficient to search, by the socket insert 17 being rotated with the insertion instrument, for a position in which all three holding claws 2 have contact with the hip socket front face. It is not necessary for the spaces between the claws 2 to be free from tissue;
the small structural height of the insertion instrument so that it projects only slightly beyond the front face of the socket insert 17 and can consequently also be packaged in existing sterile packagings for socket inserts 17 without the geometry of the packaging having to be changed;
the monolithic and simple formation of the insertion instrument which allows cost-effective production, handling and sterilisation and allows single use.

Other embodiments result by varying the formation of the annular resilient element, that is to say, the resilient support element 12. On the one hand, the basic form of the resilient support element 12, in the view from above according to FIG. 3, can be varied. On the other hand, it is conceivable to vary the form of the cross-section of the annular element or to combine both types of variation.

As a result, for example, triangular or polygonal geometries are also conceivable, cf. FIG. 7.

FIG. 7 shows two different insertion instruments when viewed from above. It is possible to vary the geometry of the annular, resilient element, for example, by means of a triangular shape (FIG. 7a) or a polygonal shape (FIG. 7b).

It is further possible to construct the direct connection paths between the three holding claws 2 by resilient path elements. If, for example, a concertina-like construction of the connection paths 13 is carried out (cf. FIG. 8), there results a deformability of the path element when a force is applied, which results in a radial displacement of the holding claws 2. In this instance, it is also possible to specifically construct the force/path characteristic of the holding claws 2 by means of the number and construction of the concertina curves.

It is further conceivable not to arrange the concertina-like formation in a plane parallel with the plane of the holding claws, but instead perpendicularly thereto, cf. FIG. 9. In order also to allow integration in existing packagings in this instance, the concertina curves are advantageously displaced structurally into the region of the spherical recess 5 of the socket insert 17.

FIG. 8 is a plan view of an insertion instrument according to the invention having a direct connection of the three holding claws 2 by means of concertina-like resilient elements or resilient support elements 12 or connection paths 13 between the claws 2.

Figure 9A:
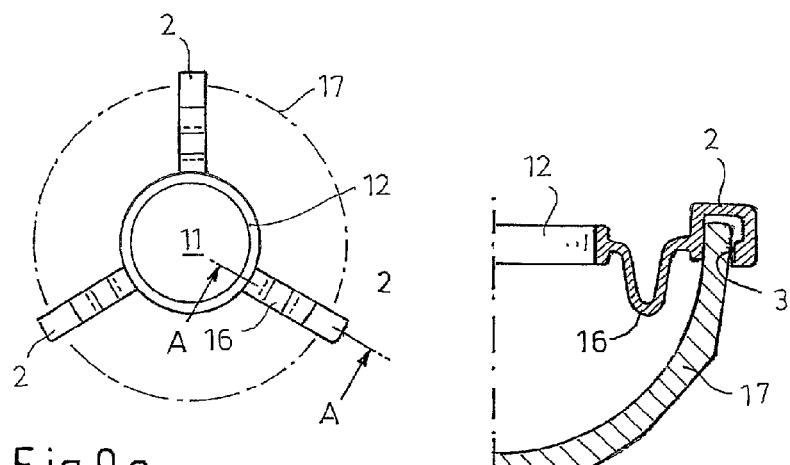
FIGS. 9a and 9b are a plan view (FIG. 9a) and a sectional view (FIG. 9b) of an insertion instrument according to the invention, respectively.
Figure 9B:
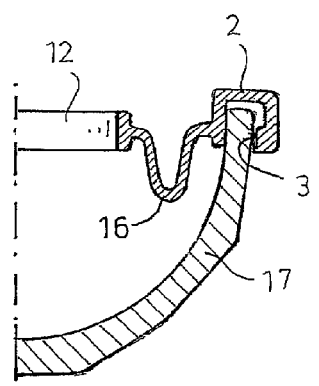

FIG. 9 is a plan view (FIG. 9a) and a sectional view (FIG. 9b) of an insertion instrument according to the invention, respectively. The three holding claws 2 are connected by means of a central ring or support element 15 by concertina-like resilient elements 16 which are arranged perpendicularly to the plane of the three holding claws 2. The holding claws 2 are secured to those resilient elements 16.

The cross-section of the annular, resilient element or the resilient support element 12 may be varied with a cyclical shape over the periphery of the annular, resilient element or resilient support element 12. For instance, the force/path characteristic of the holding claws 2 and the shape of the annular, resilient element or the resilient support element 12 can be influenced during the deformation. It is thereby also possible selectively to prevent or influence possible occurrences of torsion of the annular element during deformation, for example, if undesirable skewing of the holding claws 2 at the edge of the socket insert 17 or the hip socket 18 could occur owing to torsion.

The cross-section can be varied by changing the height and width thereof so that flexurally flexible and flexurally rigid zones are produced, for example, flexurally rigid zones in the region of the holding claws 2 and flexurally flexible zones in the region between the holding claws 2, cf. FIG. 10.

FIG. 10 shows an insertion instrument according to the invention (cut-out between two holding claws) having a varying annular cross-section—variation in height and width of the cross-section in order to produce flexurally more rigid and flexurally less rigid zones.

Figure 11:
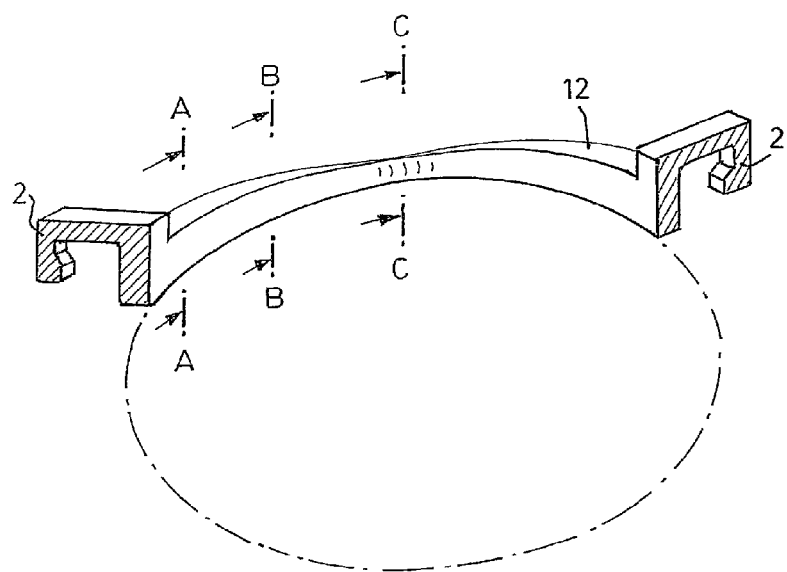
FIG. 11 shows an insertion instrument according to the invention having a varying annular cross-section.
Figure 11:
Figure 11:
Figure 11:

It is also further conceivable to have complete changes of the cross-sectional geometry over the periphery, for example, rectangular cross-section in the region of the holding claws up to a round cross-section precisely at the centre of the ring between two holding claws 2, cf. FIG. 11.

FIG. 11 shows an insertion instrument according to the invention (cut-out between two holding claws 2) having a varying annular cross-section—variation in the cross-sectional geometry from a rectangular shape to a circular shape and back to the rectangular shape.

It is also conceivable to have stepless optimisation of the cross-sectional geometry by means of finite element simulation and using so-called adaptation algorithms. The resultant geometry may deviate as desired from the initial cross-section (for example, rectangular shape or circular shape) of the optimisation but is within the correspondingly prescribed dimensional limits.

Consequently, according to the invention the insertion instrument comprises holding claws 2 which adjoin the outer side of the socket insert 17 (cf. FIG. 9) with holding faces 3 (cf. FIG. 4). The holding claws 2 are connected to resilient elements 16 which act on the holding claws 2 with force towards the interior of the socket insert 17. At the same time, the resilient elements 16 can also form the connection of the holding claws 2 with respect to each other (cf. FIGS. 3, 4, 5, 6, 7, 8, 10, 11) and/or be connected to a resilient support element 12.

It is claimed:

1. An insertion instrument for a hip endoprosthesis, comprising a plurality holding claws connected to radial resilient support elements, wherein each of the holding claws has a holding face and a lower end, wherein the insertion instrument does not have any pressure transmission devices.

2. An insertion instrument for a hip endoprosthesis, comprising a plurality holding claws which are connected via radial resilient elements to an annular support element, wherein each of the holding claws has a holding face and a lower end;
  the insertion instrument being able to be positioned on a socket insert and being able to be connected thereto by the holding claws in a clamping manner, wherein the support element surrounds a freely accessible, effective penetration face which is circular and whose center point is on a longitudinal axis of the insertion instrument;
  wherein the insertion instrument is for inserting socket inserts into endoprosthetic hip sockets;
    wherein an effective diameter of a penetration face thereof is greater than or equal to 2.0 cm, and
  wherein the insertion instrument does not have any pressure transmission devices.

3. An insertion instrument for a hip endoprosthesis, comprising a plurality holding claws which are connected via radial resilient elements to an annular support element, wherein each of the holding claws having a holding face and a lower end;
  the insertion instrument being able to be positioned on a socket insert and being able to be connected thereto by the holding claws in a clamping manner, wherein the support element surrounds a freely accessible, effective penetration face which is circular and whose center point is on a longitudinal axis of the insertion instrument;
  wherein the insertion instrument is for inserting socket inserts into endoprosthetic hip sockets; wherein an effective diameter of a penetration face thereof is 2.5 cm, and
  wherein the insertion instrument does not have any pressure transmission devices.

4. An insertion instrument according to claim 3, wherein the annular support element is a resiliently flexible ring.

5. An insertion instrument according to claim 1, wherein the instrument further comprises an annular support element and wherein the holding claws are connected to the annular support element by the radial resilient elements.

6. An insertion instrument according to claim 5, wherein the resilient elements have a shape which is arranged perpendicularly relative to a plane of the holding claws.

7. An insertion instrument for a hip endoprosthesis, comprising a plurality holding claws which are connected via radial resilient elements to an annular support element, wherein each of the holding claws has a holding face and a lower end;
  the insertion instrument being able to be positioned on a socket insert and being able to be connected thereto by the holding claws in a clamping manner, wherein the support element surrounds a freely accessible, effective penetration face which is circular and whose center point is on a longitudinal axis of the insertion instrument;
  wherein the insertion instrument is for inserting socket inserts into endoprosthetic hip sockets; wherein an effective diameter of a penetration face thereof is greater than or equal to 2.5 cm, and
  wherein the insertion instrument does not have any pressure transmission devices.

8. An insertion instrument for a hip endoprosthesis, comprising three holding claws which are connected via resilient elements to an annular support element,
  the holding claws each having a holding face;
  wherein the support element surrounds a freely accessible, effective penetration face which is circular and has a center point on a longitudinal axis of the insertion instrument, wherein the effective penetration face has an effective diameter, and wherein the effective diameter of the effective penetration face is greater than or equal to 2.5 cm, and wherein the insertion instrument does not have any pressure transmission devices.

9. An insertion instrument according to claim 8, wherein the resilient elements are arranged perpendicularly to a plane of the holding claws.

10. A combination comprising:
an insertion instrument for a hip endoprosthesis having holding claws which are connected via resilient elements to an annular support element, each of the holding claws having a holding face;
a socket insert having a spherical recess and an outer face for receiving the holding claws via a respective holding face thereof, and
wherein the insertion instrument does not have any pressure transmission devices.

11. An combination according to claim 10, wherein the holding claws fit over the outer face of the socket insert when radially expanded.

12. An insertion instrument for a hip endoprosthesis, comprising a plurality holding claws which are connected via radial resilient elements to an annular support element, wherein each of the holding claws has a holding face and a lower end;
the insertion instrument being able to be positioned on a socket insert and being able to be connected thereto by the holding claws in a clamping manner, wherein the support element surrounds a freely accessible, effective penetration face which is circular and whose center point is on a longitudinal axis of the insertion instrument;
wherein the insertion instrument is for inserting socket inserts into endoprosthetic hip sockets; wherein the support element and the resilient elements are separate components and the holding claws are connected to the support element by the resilient elements, wherein the effective penetration face has an effective diameter, and wherein the effective diameter of the effective penetration face is greater than or equal to 2.5 cm and
wherein the insertion instrument does not have any pressure transmission devices.

13. An insertion instrument for a hip endoprosthesis, comprising a plurality holding claws which are connected via radial resilient elements to an annular support element, wherein each of the holding claws having a holding face and a lower end;
the insertion instrument being able to be positioned on a socket insert and being able to be connected thereto by the holding claws in a clamping manner, wherein the support element surrounds a freely accessible, effective penetration face which is circular and whose center point is on a longitudinal axis of the insertion instrument;
wherein the insertion instrument is for inserting socket inserts into endoprosthetic hip sockets; wherein the resilient elements have a shape which is arranged perpendicularly relative to a plane of the holding claws, wherein the effective penetration face has an effective diameter, and wherein the effective diameter of the effective penetration face is greater than or equal to 2.5 cm, and
wherein the insertion instrument does not have any pressure transmission devices.

* * * * *